(12) United States Patent
Wooten, Sr. et al.

(10) Patent No.: US 7,544,161 B1
(45) Date of Patent: Jun. 9, 2009

(54) PENILE CLAMP

(76) Inventors: Horace A. Wooten, Sr., 7917 West Blvd., Inglewood, CA (US) 90305; Horace E. Wooten, 43031 Lorraine St., Lancaster, CA (US) 93534

( * ) Notice: Subject to any disclaimer, the term of this patent is extended or adjusted under 35 U.S.C. 154(b) by 453 days.

(21) Appl. No.: 11/433,715

(22) Filed: May 12, 2006

(51) Int. Cl.
*A61F 5/00* (2006.01)
(52) U.S. Cl. ........................................... 600/38
(58) Field of Classification Search ............ 600/38–41, 600/29–32; 128/885, DIG. 25
See application file for complete search history.

(56) References Cited

U.S. PATENT DOCUMENTS

| 5,388,598 | A | * | 2/1995 | Whitten | 132/275 |
| 5,778,904 | A | * | 7/1998 | Elsner | 132/275 |
| 5,855,548 | A | * | 1/1999 | Place | 600/38 |
| 5,921,914 | A | * | 7/1999 | Tucker et al. | 600/38 |
| 6,579,229 | B1 | * | 6/2003 | Nan | 600/38 |

* cited by examiner

*Primary Examiner*—Samuel G Gilbert

(57) ABSTRACT

A penile clamp is disclosed. The penile clamp includes a clamp band having a loop segment, at least one spherical terminal bead provided on the clamp band and at least one lock collar provided on the clamp band between the at least one terminal bead and the loop segment.

7 Claims, 3 Drawing Sheets

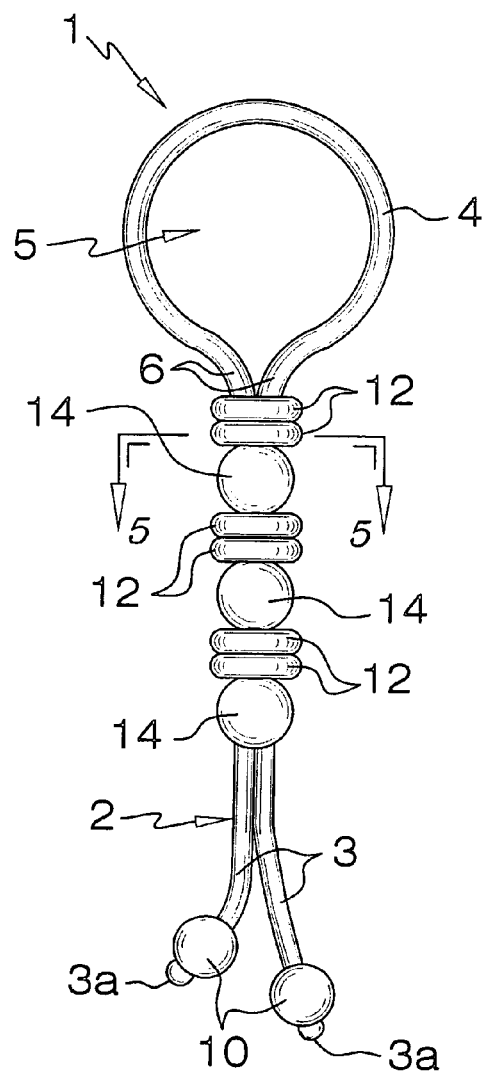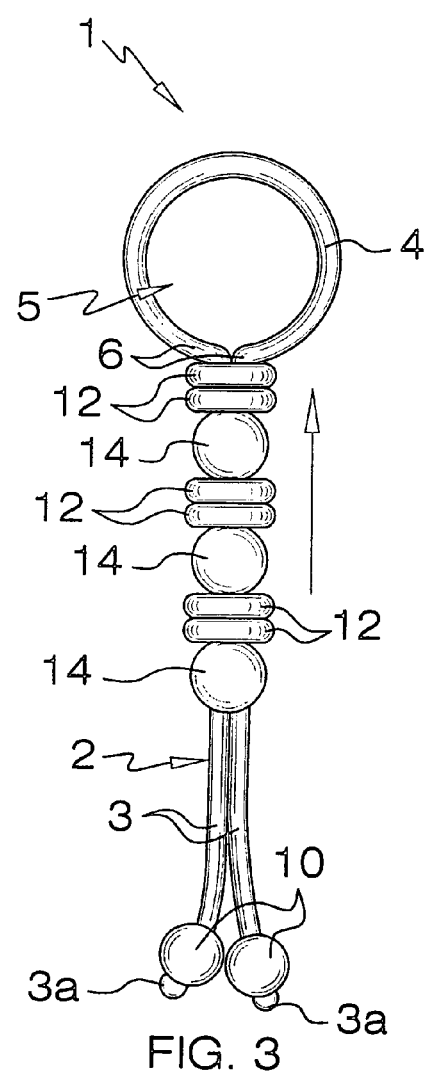
FIG. 2
FIG. 3

PENILE CLAMP

FIELD

The present invention relates to impotence-treatment devices. More particularly, the present invention relates to a penile clamp which is effective in improving an erection in persons who suffer from erectile impotence.

BACKGROUND

Erectile impotence is a common problem for men. Impotence is characterized by an inability to achieve and/or maintain a penile erection for the purpose of participating in sexual activity. Typically, impotence is caused by physiological and/or psychological conditions. Many devices known in the art for treating or overcoming the effects of impotence include pumps and implants which are complicated and must be surgically implanted.

SUMMARY

The present invention is generally directed to a penile clamp. An illustrative embodiment of the penile clamp includes a clamp band having a loop segment, at least one spherical terminal bead provided on the clamp band and at least one lock collar provided on the clamp band between the at least one terminal bead and the loop segment.

BRIEF DESCRIPTION OF THE DRAWINGS

The invention will now be described, by way of example, with reference to the accompanying drawings, in which:

FIG. 2 is a front view of an illustrative embodiment of a penile clamp, shown in a loosened configuration;

FIG. 3 is a front view of an illustrative embodiment of a penile clamp, shown in a tightened configuration;

DETAILED DESCRIPTION

Figure 1:
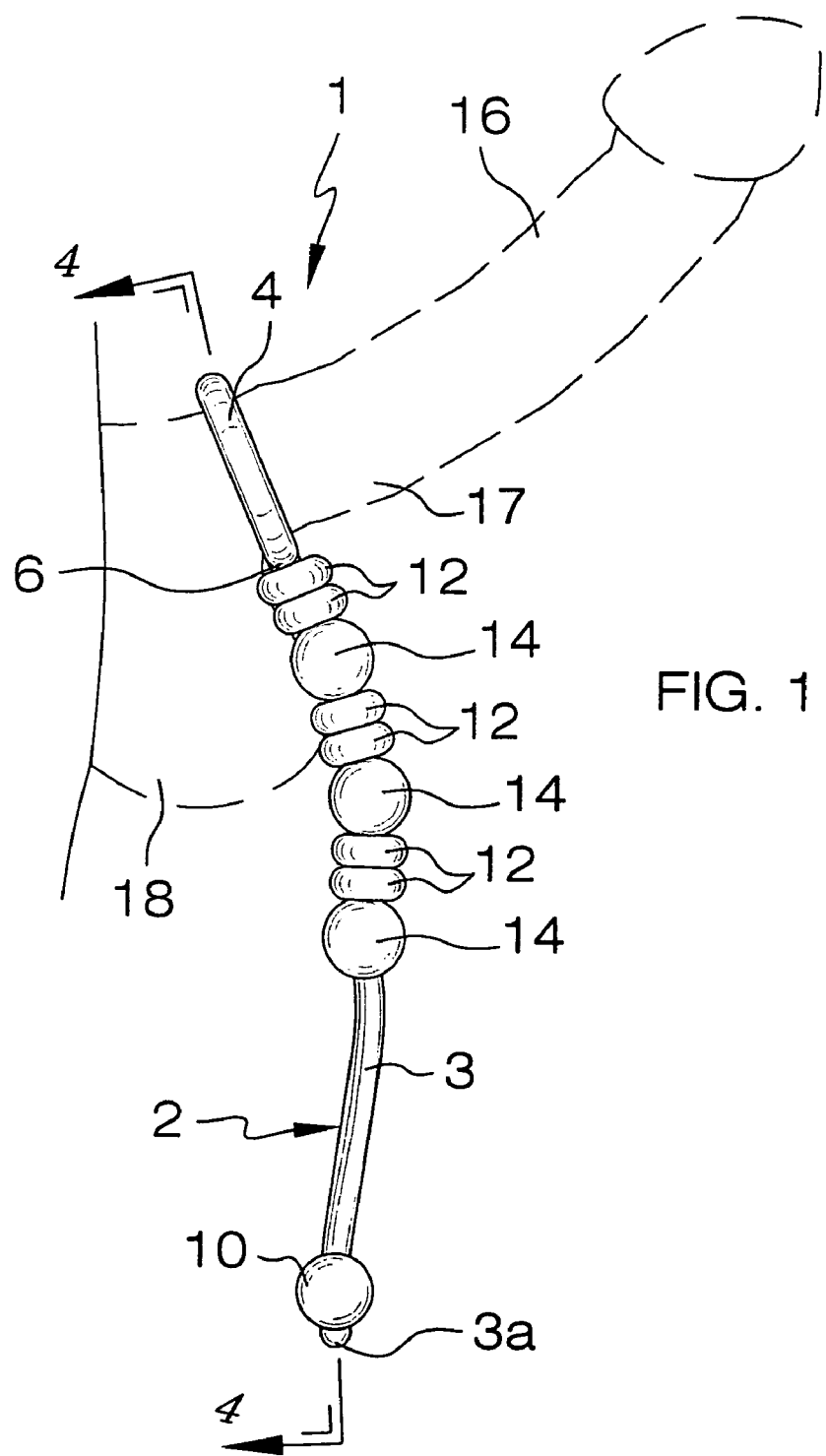
FIG. 1 is a side view of an illustrative embodiment of a penile clamp, attached to a penis in typical application of the penile clamp.

Referring initially to FIGS. 2-5 of the drawings, an illustrative embodiment of a penile clamp according to the present invention is generally indicated by reference numeral 1. The penile clamp 1 includes an elongated clamp band 2 which may be continuous. In some embodiments, the clamp band 2 is a durable, flexible material such as rubber or flexible plastic and may have a solid construction. In other embodiments, the clamp band 2 is a wire strand such as 14-gage wire, for example. The clamp band 2 includes a pair of generally elongated, parallel lock segments 3 and a generally annular or circular loop segment 4 which extends from the lock segments 3 at a pair of bends 6. Accordingly, the clamp band 2 is generally symmetrical with respect to a plane (not shown) which extends through the loop segment 4 and between the lock segments 3 of the clamp band 2. A loop opening 5 extends through the loop segment 4 of the clamp band 2.

Figure 4:
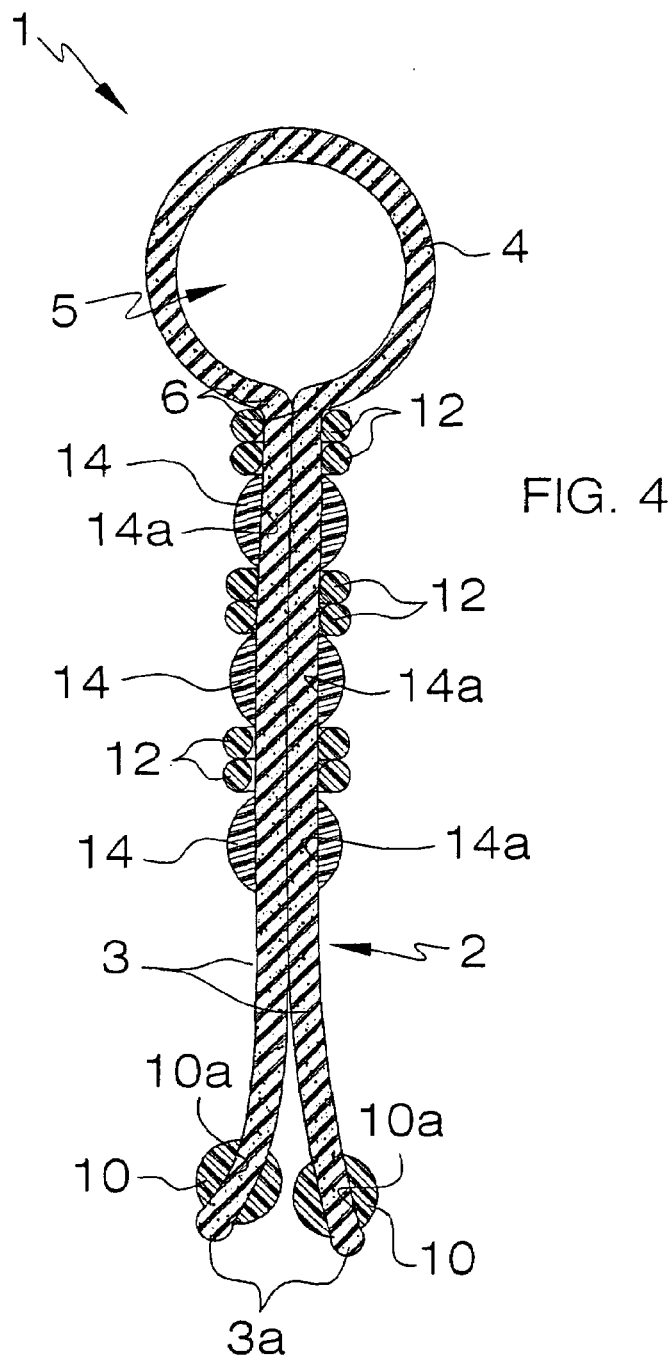
FIG. 4 is a sectional view, taken along section lines 4-4 in FIG. 1, of an illustrative embodiment of a penile clamp.

A terminal bead 10 is provided on at least one of the lock segments 3 of the clamp band 2, in spaced-apart relationship to the loop segment 4, for purposes which will be hereinafter described. As shown in FIGS. 2-4, a terminal bead 10 may be provided on each of the lock segments 3, typically adjacent to the respective ends of the clamp band 2. Each terminal bead 10 may have a generally spherical shape. As shown in FIG. 4, a bead opening 10a typically extends through each terminal bead 10. Each lock segment 3 of the clamp band 2 extends through the band opening 10a of the corresponding terminal bead 10. A segment expansion 3a, the diameter or width of which is greater than that of the bead opening 10a, may be provided in the end of each lock segment 3 to prevent the terminal beads 10 from inadvertently sliding off the respective lock segments 3. Alternatively or additionally, the terminal beads 10 may be secured to the respective lock segments 3 using any of a variety of techniques known to those skilled in the art.

Figure 5:
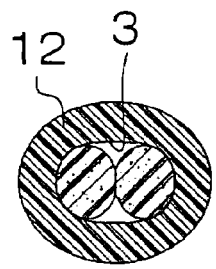
FIG. 5 is a cross-sectional view, taken along section lines 5-5 in FIG. 2, of an illustrative embodiment of a penile clamp.

At least one lock collar 12 slidably engages the lock segments 3 of the clamp band 2, between the loop segment 4 and the terminal bead or beads 10. As shown in FIGS. 2-4, multiple lock collars 12 may slidably engage the lock segments 3. Multiple pairs of adjacent lock collars 12 may slidably engage the lock segments 3. Each lock collar 12 may be a rubber or plastic washer, for example. As shown in FIG. 5, a lock collar opening 13 extends through each lock collar 12. The lock segments 3 of the clamp band 2 extend through the lock collar opening 13 of each lock collar 12, in adjacent relationship to each other. At least one segment bead 14 may slidably engage the lock segments 3 of the clamp band 2. As shown in FIG. 4, each segment bead 14 typically includes a segment bead opening 14a through which the lock segments 3 extend. Multiple segment beads 14 may slidably engage the lock segments 3, with each segment bead 14 between adjacent pairs of lock collars 12. The segment beads 14 may be provided on the lock segments 3 in alternating relationship to the lock collars 12. Accordingly, the lock collar or lock collars 12, in concert with the segment bead or beads 14, can be slidably displaced away from the terminal bead or beads 10, as indicated by the arrow in FIG. 3, to progressively decrease the diameter of the loop opening 5 of the loop segment 4 by drawing the lock segments 3 against each other at the bends 6. Conversely, the lock collar or lock collars 12, in concert with the segment bead or beads 14, can be slidably displaced toward the terminal bead or beads 10, as shown in FIG. 2, to progressively increase the diameter of the loop opening 5 of the loop segment 4. The terminal bead or beads 10 prevent(s) the lock collar or lock collars 12 from inadvertently sliding off the lock segments 3 of the clamp band 2.

Referring next to FIG. 1 of the drawings, in typical use, the penile clamp 1 is suitable for maintaining an erection during sexual activity. Accordingly, the diameter of the loop opening 5 (FIG. 2) of the clamp band 2 is initially adjusted to an appropriate size which facilitates placement of the clamp band 2 around the penis 16 of a male user of the penile clamp 1. Adjustment of the diameter of the loop opening 5 is facilitated by sliding the lock collar or lock collars 12, in concert with the segment bead or beads 14, along the lock segments 3 of the clamp band 2. After the diameter of the loop opening 5 is adjusted to the appropriate size, the clamp band 2 is placed on the user's penis 16 as the loop opening 5 receives the penis 16, until the clamp band 2 is positioned at the base 17 of the penis 16, adjacent to the scrotum 18. As the firmness of the erection of the user's penis 16 increases, the diameter of the loop opening 5 is decreased and the loop segment 4 tightened against the penis 16, by sliding the lock collar or lock collars 12 and segment bead or beads 14 away from the terminal bead or beads 10. This tightening of the loop segment 4 around the penis 16 constricts the penis 16, and therefore, restricts the flow of blood out of the penis 16. Natural friction between the lock collar 12 or lock collars 12 and the lock segments 3 of the clamp band 2 prevents the lock collar or lock collars 12 from inadvertently sliding on the lock segments 3 and loosening the loop segment 4 on the penis 16 during sexual activity. During sexual activity, the lock collar or collars 12 adjacent to the bends 6 of the loop segment 4 typically impart additional sensation to the base 17 of the penis 16. At the conclusion of the sexual activity, the penile clamp 1 is released by sliding the lock collar or lock collars 12 on the lock segments 3, toward the terminal bead or beads 10, thereby loosening the clamp band 2 on the penis 16 and facilitating removal of the clamp band 2 from the penis 16.

While the preferred embodiments of the invention have been described above, it will be recognized and understood that various modifications can be made in the invention and the appended claims are intended to cover all such modifications which may fall within the spirit and scope of the invention.

What is claimed is:

1. A penile clamp, comprising:
   a generally symmetrical, flexible, wire clamp band having a loop segment;
   at least one spherical terminal bead carried by said clamp band;
   at least one lock collar slidably engaging said clamp band between said at least one terminal bead and said loop segment; and
   at least one segment bead slidably engaging said clamp band between said at least one terminal bead and said loop segment.

2. The penile clamp of claim 1 wherein said at least one terminal bead comprises a plurality of terminal beads.

3. The penile clamp of claim 1 wherein said at least one lock collar comprises a plurality of paired lock collars.

4. The penile clamp of claim 1 wherein said at least one lock collar comprises a lock collar opening and wherein said clamp band extends through said lock collar opening.

5. The penile clamp of claim 1 wherein said clamp band comprises a pair of generally elongated, parallel lock segments extending from said loop segment.

6. The penile clamp of claim 5 wherein said at least one terminal bead comprises a pair of terminal beads carried by said pair of lock segments, respectively.

7. The penile clamp of claim 5 wherein said at least one lock collar slidably engages said pair of lock segments.

\* \* \* \* \*